United States Patent [19]

Allway

[11] Patent Number: 5,491,049
[45] Date of Patent: Feb. 13, 1996

[54] PHOTOGRAPHIC COLOUR COUPLERS, METHODS OF MAKING THEM AND PHOTOGRAPHIC MATERIALS CONTAINING THEM

[75] Inventor: Philip A. Allway, Watford, United Kingdom

[73] Assignee: Eastman Kodak Company, Rochester, N.Y.

[21] Appl. No.: 238,134

[22] Filed: May 4, 1994

[51] Int. Cl.⁶ ........................................ G03C 7/36
[52] U.S. Cl. .................. 430/379; 430/386; 430/387; 430/543; 430/558
[58] Field of Search ..................... 430/543, 558, 430/555, 386, 387, 379

[56] References Cited

U.S. PATENT DOCUMENTS 5,162,196  11/1992  Sato et al. ........................... 430/384

FOREIGN PATENT DOCUMENTS

| | | |
|---|---|---|
| 0369297 | 7/1989 | European Pat. Off. . |
| 9209010 | 5/1992 | WIPO . |
| 92/14189 | 8/1992 | WIPO . |
| 9301523 | 1/1993 | WIPO . |
| 9307534 | 4/1993 | WIPO . |

*Primary Examiner*—Lee C. Wright
*Attorney, Agent, or Firm*—Arthur E. Kluegel

[57] ABSTRACT

The present invention provides a photographic element comprising a support, at least one photosensitive silver halide layer and in or adjacent said silver halide layer a colour coupler of one of the general formulas:

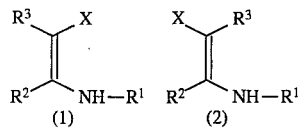

wherein
- $R^1$ is a subsituted or unsubstituted aryl or a subsituted or unsubstituted heterocylic group,
- $R^2$ is a subsituted or unsubstituted, saturated or unsaturated, primary or secondary alkyl group in which the carbon atom which joins $R^2$ to rest of the coupler has at least one fluorine atom attached to it,
- $R^3$ is an electron-withdrawing group, and
- X is H or a coupling-off group, and wherein the electron-withdrawing properties of $R^1$ are such that the dye formed on coupling with oxidised colour developing agent 4-(N-ethyl-N-2-hydroxyethyl)-2-methylphenylenediamine has a $\lambda_{max}$ of from 537 to 570 nm.

The invention also includes the coupler composition, methods of synthesizing the coupler and a method of forming an image in a photographic element.

9 Claims, No Drawings

PHOTOGRAPHIC COLOUR COUPLERS, METHODS OF MAKING THEM AND PHOTOGRAPHIC MATERIALS CONTAINING THEM

FIELD OF THE INVENTION

This invention relates to photographic colour couplers and in particular to a class of magenta couplers.

BACKGROUND OF THE INVENTION

Colour couplers are known to belong to a number of classes, for example magenta dye-forming couplers can be pyrazolones, pyrazolotriazoles and pyrazolobenzimidazoles while yellow dye-forming couplers can be acetanilides.
Problem to be Solved by the Invention
There is always a need for new classes of couplers that have advantages over those already known to the art.

SUMMARY OF THE INVENTION

According to the present invention there is provided a photographic element comprising a support, at least one photosensitive silver halide layer and in or adjacent said silver halide layer a colour coupler of one of the general formulas:

$$\underset{(1)}{\overset{R^3}{\underset{R^2}{\diagdown}}\!\!\!>\!\!=\!\!<\!\!\underset{NH-R^1}{\overset{X}{\diagup}}} \quad \underset{(2)}{\overset{X}{\underset{R^2}{\diagdown}}\!\!\!>\!\!=\!\!<\!\!\underset{NH-R^1}{\overset{R^3}{\diagup}}}$$

wherein $R^1$ is a subsituted or unsubstituted aryl or a subsituted or unsubstituted heterocylic group, $R^2$ is a subsituted or unsubstituted, saturated or unsaturated, primary or secondary alkyl group in which the carbon atom which joins $R^2$ to rest of the coupler has at least one fluorine atom attached to it, $R^3$ is an electron-withdrawing group, and X is H or a coupling-off group, and wherein the electron-withdrawing properties of $R^1$ are such that the dye formed on coupling with oxidised colour developing agent 4-(N-ethyl-N-2-hydroxyethyl)-2-methylphenylenediamine has a $\lambda_{max}$ of from 537 to 570 nm.

The invention also includes the coupler composition, methods of synthesizing the coupler and a method of forming an image in a photographic element.
Advantageous Effect of the Invention
The present invention provides a new class of couplers capable of forming magenta dyes having desirable spectral characteristics having maximum wavelength ($\lambda_{max}$) in the range from 537 to 570 nm.

DETAILED DESCRIPTION OF THE INVENTION

It is preferred that when $R^1$ is a substituted group the substituents are electron-withdrawing substituents. Examples of such substituent groups are listed below under $R^3$. Particularly preferred electron-withdrawing substituents for $R^1$ are cyano, nitro, alkylsulphonyl and arylsulphonyl.

Examples of groups which $R^2$ may represent are trifluoromethyl, 2,2,2-trifluoroethyl, nonafluorobutyl and trifluoroethylene groups.

$R^3$ may be an electron withdrawing group wherein the value of the Hammett substituent constant $\sigma_p$ (SIGMA$_p$ as defined by Hansch et al, J. Med. Chem., 1973, 16, 1207; and ibid. 1977, 20, 304) is 0.03 or greater, preferably 0.35 or greater and more preferably 0.5 or above.

A substituent or atom wherein the value of the $\sigma_p$ (SIGMA$_p$) is 0.03 or above includes a fluorine atom, a chlorine atom, a bromine atom an iodine atom, a substituted alkyl group (e.g. trichloromethyl, trifluoromethyl, chloromethyl and perfluorobutyl), a nitrile group, an acyl group (e.g. formyl, acetyl and benzoyl), a carboxyl group, a substituted or unsubstituted carbamoyl group (e.g. methylcarbamoyl) an aromatic group substituted by another electron attractive group (e.g. pentachlorophenyl, pentafluorophenyl), a heterocyclic group which may be substituted (e.g. 2-thienyl, 2-benzoxazolyl, 2-benzthiazolyl, 1-tetrazolyl and 1-phenyl-2-benzimidazolyl), a nitro group, an azo group (e.g. phenylazo), an amino group substituted by another electron attractive group (e.g. ditrifluoromethylamino), an alkoxy group substituted by another electron attractive group (e.g. trifluoromethoxy), an alkylsulphonyloxy group (e.g. methanesulphonyloxy), an acyloxy group (e.g. acetyloxy, benzoyloxy), an arylsulphonyloxy group (e.g. benzenesulphonyloxy), a phosphoryl group (e.g. dimethoxyphosphoryl and diphenylphosphoryl), a thioalkyl group substituted by another electron attractive group (e.g. trifluoromethyl), a sulphamoyl group, a sulphonamide group, a sulphonyl group (e.g. methanesulphonyl, benzenesulphonyl), a thiocyanate, sulphoxide, carbonamido, alkyloxycarbonyl, aryloxycarbonyl, alkylsulphoxyl, arylsulphoxyl, sulphonamido, sulphonato group or a substituted phosphorus atom.

Examples of electron-withdrawing groups which $R^3$ may represent are hydrogen, halogen, —CN, —NO$_2$, —OR$^4$, —SR$^4$, —SO$_2$R$^5$, —OSO$_2$R$^5$, —SOR$^5$, —NHCOR$^5$, —CONHR$^5$, —OCONHR$^5$, —NHCO—OR$^5$, —SO$_2$NH—R$^5$, —NHSO$_2$R$_5$, —NHSO$_2$NHR$^5$, —NHNH—SO$_2$—R$^5$, —COOH, —COOR$^5$, —O—COR$^5$, —COR$^5$, —CSR$^5$, —CONHNHR$^5$, —CF$_3$, —NH$_2$, —NHR$^5$, —NHR$^5$R$^{5'}$, silyloxy, aryl, aralkyl, alkyl, cycloalkyl, ureido, imido, or a heterocycle, wherein $R^5$ is an alkyl, cycloalkyl, aryl or heterocyclic group any of which may be substituted, $R^{5'}$ has the same definition as $R^5$ and may be the same or different to $R^5$, and $R^4$ is an alkyl, cycloalkyl, aryl or heterocyclic group any of which are optionally substituted, and wherein the nature of the groups $R^5$, $R^{5'}$ and $R^4$ and the substituents thereon are such that the group is electron-withdrawing.

Coupling-off groups (X) are well known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation, color correction and the like.

Examples of coupling-off groups include chloro, alkoxy, aryloxy (e.g. phenyloxy or 2-chloro-, 2,3,5-isopropyl-, 4-carboxy-, 4-carboxy-2-methyl-carbonamido, 4-nitro-2-carbamoyl-phenyloxy), alkylthio, arylthio (e.g. phenylthio, or 2,3,5-isopropyl-phenylthio), heteroyloxy (e.g. pyridyloxy), sulfonyloxy, acyloxy, carboxy, acyl, heterocyclyl joined via a ring carbon or hetero atom in the heterocyclic nucleus, sulfonamido, mercaptotetrazole, mercaptopropionic acid, phosphonyloxy and arylazo (e.g. 4-hydroxy-, 4-hexadecyloxy- 3-methoxy-, 4-methyl-2-hydroxy-, 4-methylsulphonyl- or 4-t-butylcarbonamido-phenylazo).

Examples of coupling-off groups containing photographically useful groups (PUG's) are listed Table 1 below.

TABLE 1

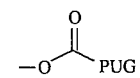

The present couplers may contain a ballast group of such size and configuration that the coupler is rendered non-diffusible in photographic layers. Such a ballast may form part of $R^1$, $R^2$ or $R^3$.

The present invention further provides a photographic element comprising a support, at least one photosensitive silver halide layer and associated therewith a colour coupler of the present invention.

The present invention also provides a method by which the present couplers may be prepared in which the starting compound:

 (3)

is reacted with a compound which is capable of combining with the oxygen of the starting compound to form a leaving group thus forming a compound of the formula (1) or (2) above wherein X is H. In one embodiment the reaction scheme is as follows:

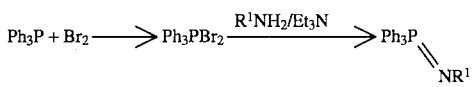

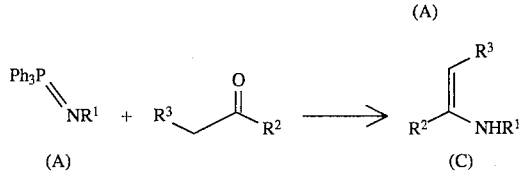

In another embodiment the reaction scheme is as follows:

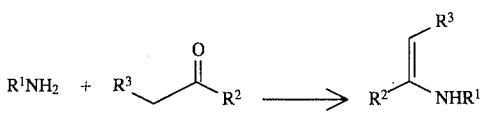

When it is desired to introduce a coupling-off group, the compound in which X is H is reacted with a compound which is a source of the coupling-off group as an electrophile or the starting compound (3) in the scheme above has the carbon between the carbon atom of the carbonyl group and $R^3$ substituted with the coupling-off group.

Specific examples of couplers according to the present invention are listed below in Table 2.

TABLE 2

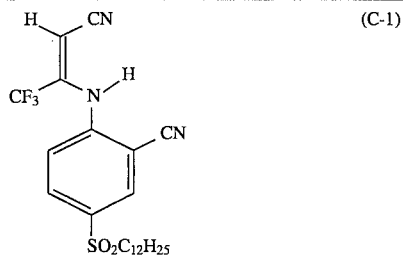 (C-1)

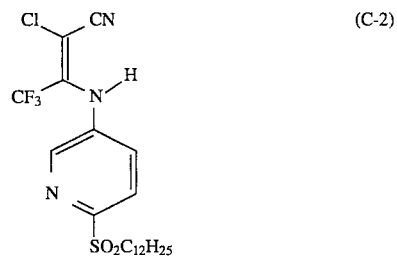 (C-2)

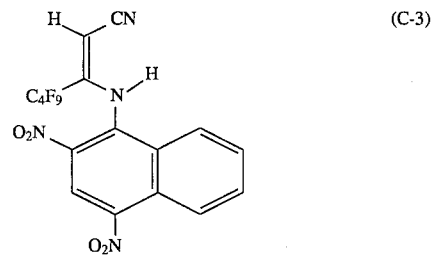 (C-3)

TABLE 2-continued
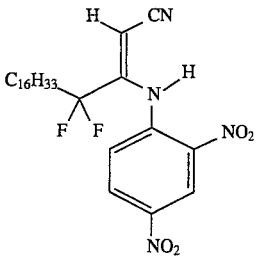  (C-4)
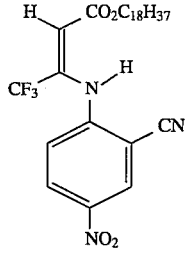  (C-5)
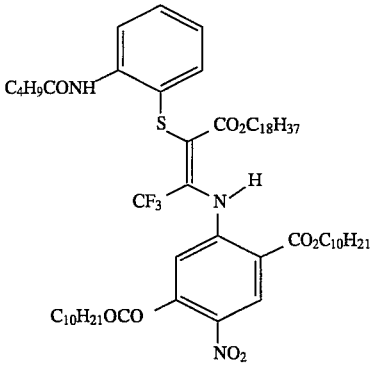  (C-6)
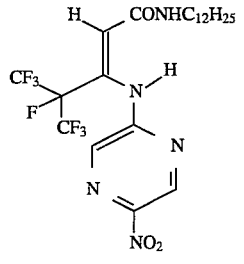  (C-7)
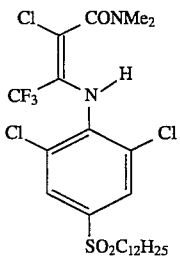  (C-8)
TABLE 2-continued
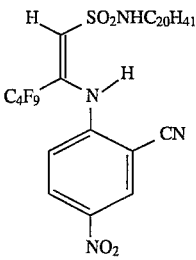  (C-9)
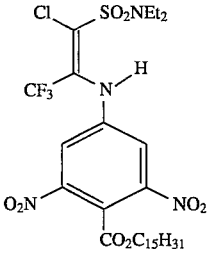  (C-10)
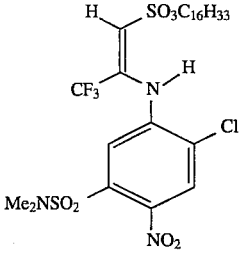  (C-11)
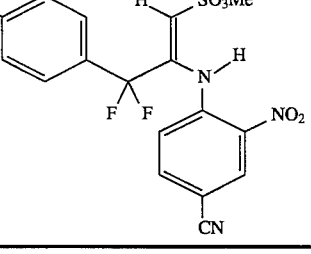  (C-12)
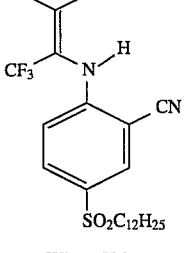
Where X is:
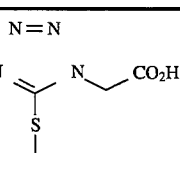  C-13
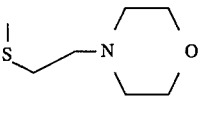  C-14

TABLE 2-continued

| Structure | Label |
|---|---|
| —S—CH₂CO₂C₁₂H₂₅-n | C-15 |
| 2,4,6-tri(i-Pr)phenyl-S— | C-16 |
| 2-pyridyloxy— (—O-2-pyridyl) | C-17 |
| 4-(CO₂H)phenoxy— | C-18 |
| 2-(NHCOCH₃)-4-methylphenoxy— | C-19 |
| 2-(CONH₂)-5-(NO₂)phenoxy— | C-20 |
| —OC₁₂H₂₅-n | C-21 |
| —O(CH₂)₂OC₂H₅ | C-22 |
| —OC₁₆H₃₃-n | C-23 |
| —O(CH₂)₂CONH(CH₂)₂OCH₃ | C-24 |
| —N(SO₂CH₃)C(CH₃)₃ | C-25 |
| 3-methyl-uracil-N-yl (C-26 structure) | C-26 |
| 2-oxo-1-pyridyl | C-27 |
| 1-benzyl-hydantoin-N-yl | C-28 |
| 4-(4-OH-phenyl)azo— | C-29 |
| 4-(3-OCH₃-4-OC₁₂H₂₅-n-phenyl)azo— | C-30 |
| 4-(2-OH-4-methylphenyl)azo— | C-31 |
| C-32 (naphthalene disulfonate azo dye) | C-32 |

TABLE 2-continued

| | |
|---|---|
| (structure: phenyl-N=N- with para-SO₂CH₃) | C-33 |
| (structure: phenyl-N=N- with para-NHCOBu-t) | C-34 |
| (structure: CH₃S-C(=N-N)-N(Et)-) | C-35 |
| (structure: CF₃/X substituted enamine with CO₂C₁₈H₃₇, attached to 2-CN-4-NO₂-phenyl-NH) | |
| Where X is: | |
| CH₃S-C(=N-N)-N(CH₂CO₂H)- | C-36 |
| CH₃S-CH₂CH₂-morpholine | C-37 |
| CH₃S-CH₂-CO₂C₁₂H₂₅-n | C-38 |
| 2,4,6-tri-i-Pr-phenyl-S- | C-39 |

TABLE 2-continued

| | |
|---|---|
| 2-oxy-pyridine | C-40 |
| 4-oxy-benzoic acid | C-41 |
| 2-oxy-3-NHCOCH₃-5-CH₃-phenyl | C-42 |
| 2-oxy-5-NO₂-phenyl-CONH₂ | C-43 |
| OC₁₂H₂₅-n | C-44 |
| O(CH₂)₂OC₂H₅ | C-45 |
| OC₁₆H₃₃-n | C-46 |
| O(CH₂)₂CONH(CH₂)₂OCH₃ | C-47 |
| C(CH₃)₂-NSO₂CH₃ | C-48 |
| (6-methyl uracil N-yl) | C-49 |
| 2-oxo-pyridin-1-yl | C-50 |
| 3-benzyl-hydantoin-1-yl | C-51 |

TABLE 2-continued
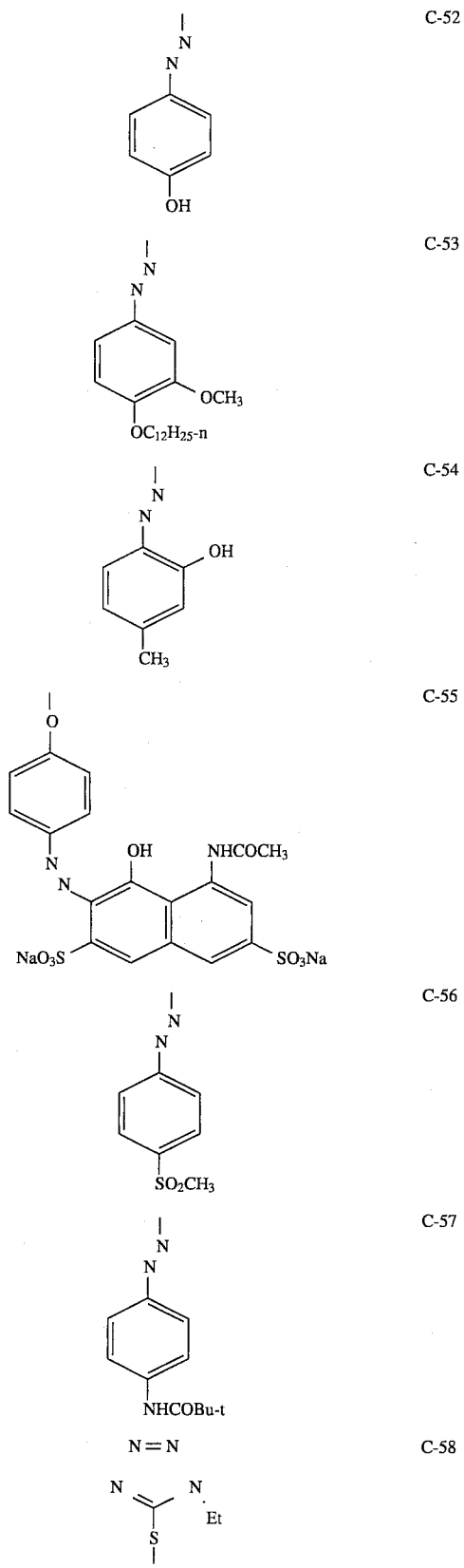
TABLE 2-continued
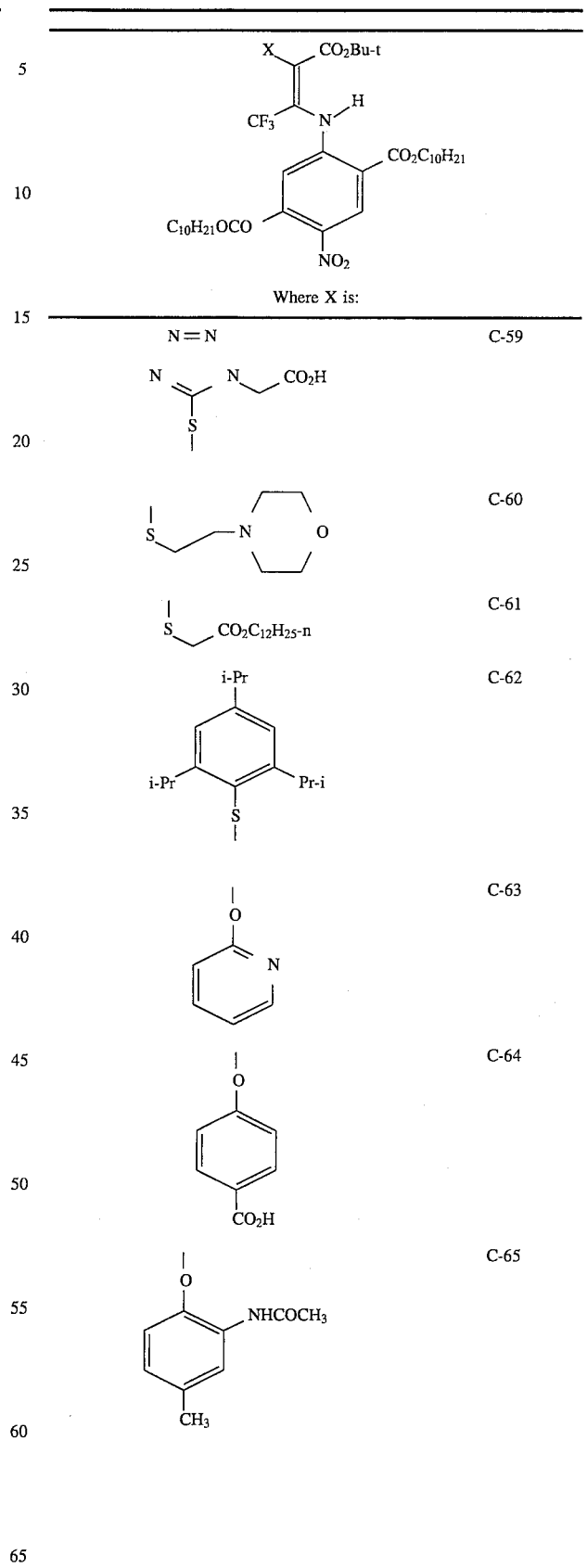

TABLE 2-continued
| | |
|---|---|
| 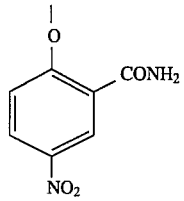 | C-66 |
| OC₁₂H₂₅-n (attached) | C-67 |
| O(CH₂)₂OC₂H₅ (attached) | C-68 |
| OC₁₆H₃₃-n (attached) | C-69 |
| O(CH₂)₂CONH(CH₂)₂OCH₃ (attached) | C-70 |
| 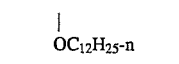 | C-71 |
| 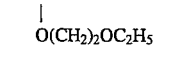 | C-72 |
| 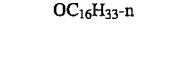 | C-73 |
| 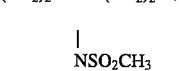 | C-74 |
|  | C-75 |
| 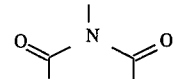 | C-76 |
| 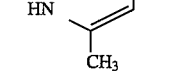 | C-77 |
| 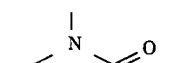 | C-78 |
| 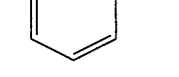 | C-79 |
| 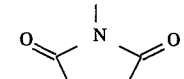 | C-80 |
| 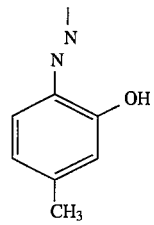 | C-81 |
Where X is:
| | |
|---|---|
| 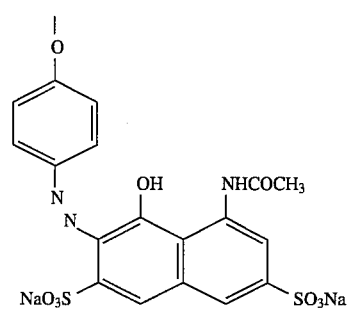 | C-82 |

TABLE 2-continued

| Structure | Label |
|---|---|
| (methylthio-ethyl morpholine) | C-83 |
| S-CH₂-CO₂C₁₂H₂₅-n | C-84 |
| 2,4,6-tri(i-Pr)phenyl-S- | C-85 |
| 2-pyridyloxy | C-86 |
| 4-carboxyphenoxy | C-87 |
| 2-(NHCOCH₃)-4-methylphenoxy | C-88 |
| 2-CONH₂-5-NO₂-phenoxy | C-89 |
| OC₁₂H₂₅-n | C-90 |
| O(CH₂)₂OC₂H₅ | C-91 |
| OC₁₆H₃₃-n | C-92 |
| O(CH₂)₂CONH(CH₂)₂OCH₃ | C-93 |
| t-Bu-NSO₂CH₃ | C-94 |
| uracil-methyl derivative | C-95 |
| N-methyl-2-pyridone | C-96 |
| benzyl-N-imidazolidinedione | C-97 |
| 4-hydroxyphenylazo-N-methyl | C-98 |
| 3-OCH₃-4-OC₁₂H₂₅-n-phenylazo-N-methyl | C-99 |
| 2-OH-4-methylphenylazo-N-methyl | C-100 |
| naphthol azo dye (disulfonate) | C-101 |

TABLE 2-continued (Chemical structures for C-102 through C-120)

- C-102: 4-(methylsulfonyl)phenyl-N=N–
- C-103: 4-(NHCOBu-t)phenyl-N=N–
- C-104: N=N / N–SMe / N–Et Where X is:
- C-105: –N(CH₂CO₂H)–C(SMe)=N–N=
- C-106: –S–CH₂CH₂–N(morpholino)
- C-107: –S–CH₂–CO₂C₁₂H₂₅-n
- C-108: –S–(2,4,6-tri-isopropylphenyl)

- C-109: –O–(2-pyridyl)
- C-110: –O–C₆H₄–CO₂H (para)
- C-111: –O–(2-NHCOCH₃-5-methyl-phenyl)
- C-112: –O–(2-CONH₂-4-NO₂-phenyl)
- C-113: –OC₁₂H₂₅-n
- C-114: –O(CH₂)₂OC₂H₅
- C-115: –OC₁₆H₃₃-n
- C-116: –O(CH₂)₂CONH(CH₂)₂OCH₃
- C-117: –NSO₂CH₃ on t-butyl
- C-118: hydantoin-type ring with CH₃
- C-119: 2-oxo-pyridin-1-yl
- C-120: 1-benzyl-hydantoin type TABLE 2-continued
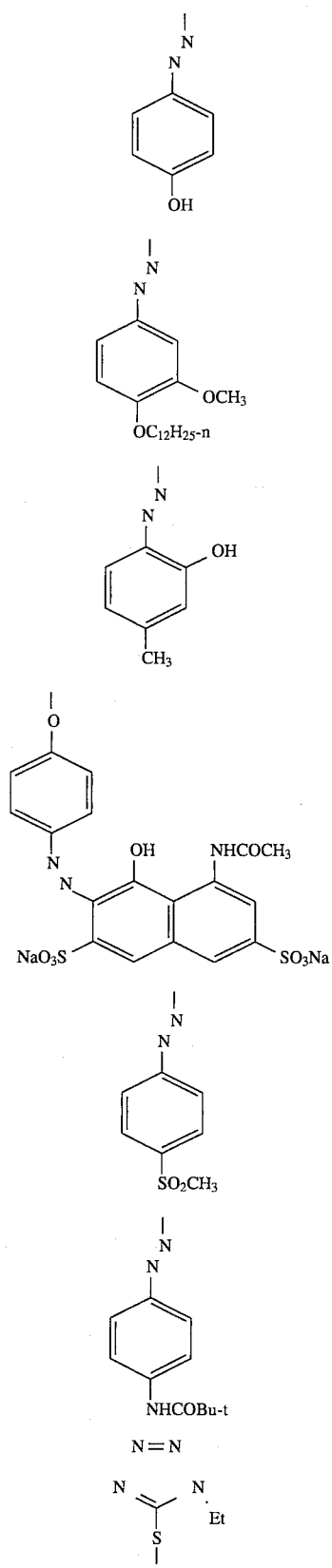
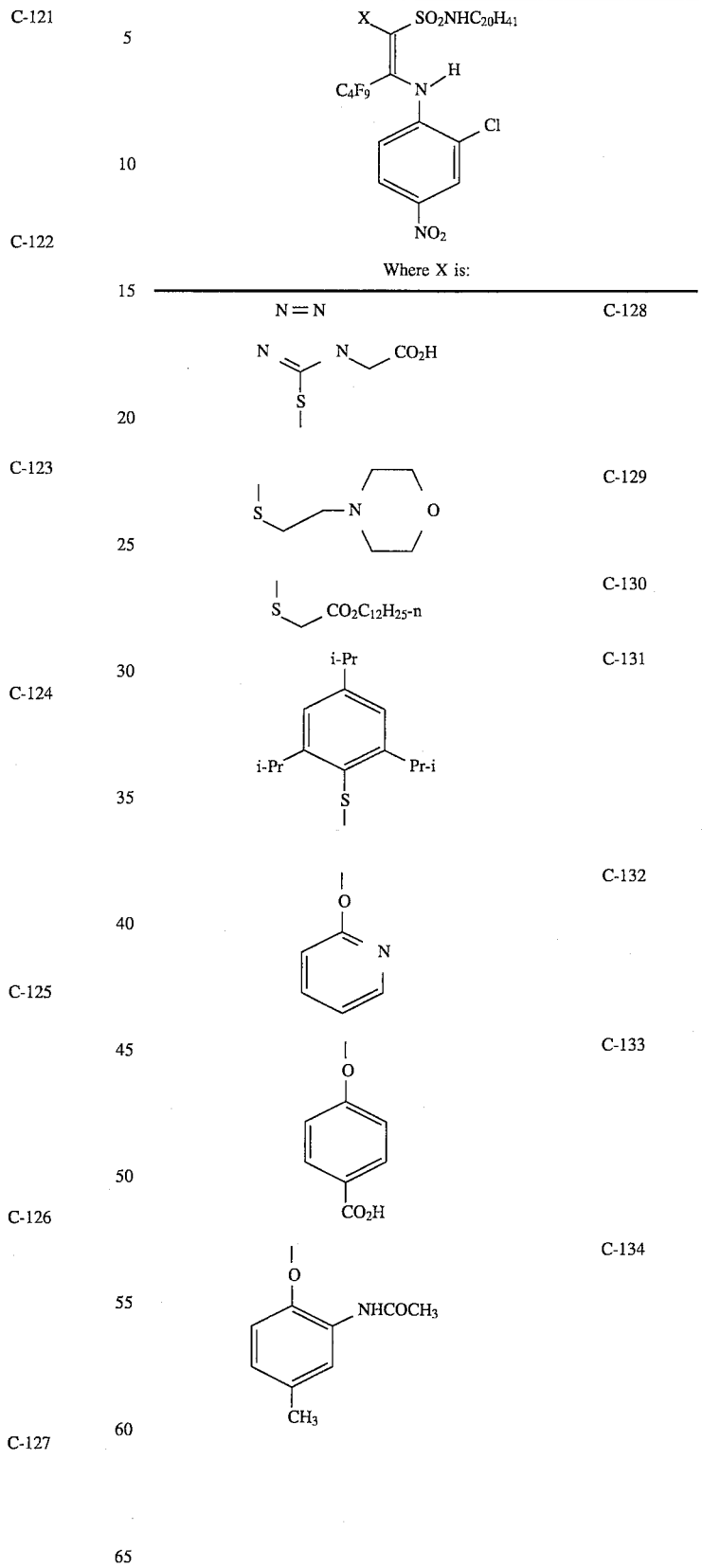

TABLE 2-continued
| | |
|---|---|
| 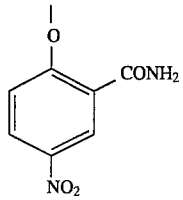 | C-135 |
| OC₁₂H₂₅-n | C-136 |
| O(CH₂)₂OC₂H₅ | C-137 |
| OC₁₆H₃₃-n | C-138 |
| O(CH₂)₂CONH(CH₂)₂OCH₃ | C-139 |
| 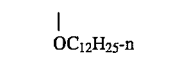 | C-140 |
| 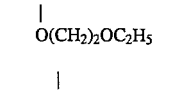 | C-141 |
| 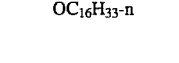 | C-142 |
| 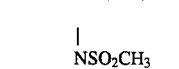 | C-143 |
| 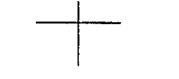 | C-144 |
| 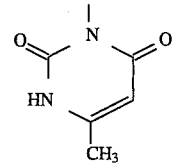 | C-145 |
TABLE 2-continued
| | |
|---|---|
| 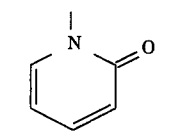 | C-146 |
| 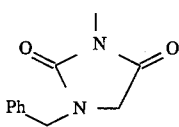 | C-147 |
| 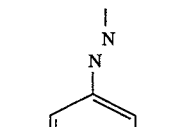 | C-148 |
| 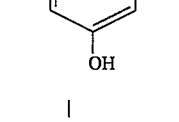 | C-149 |
| 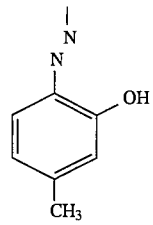 | C-150 |
| 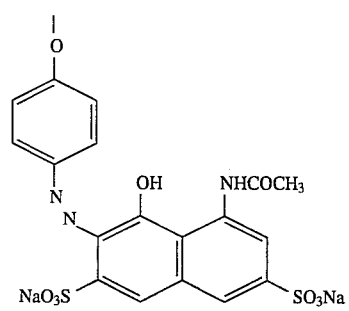 | |
| Where X is: | |
| 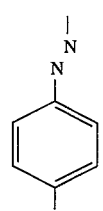 | C-151 |

TABLE 2-continued
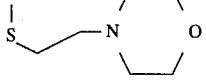 C-152
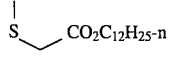 C-153
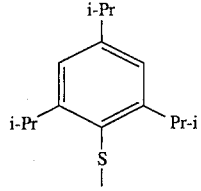 C-154
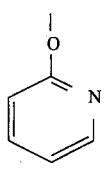 C-155
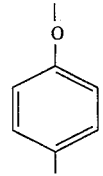 C-156
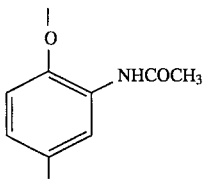 C-157
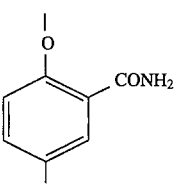 C-158
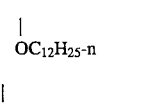 C-159
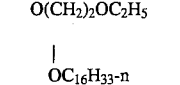 C-160
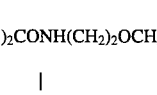 C-161
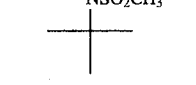 C-162
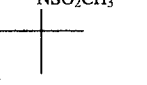 C-163
TABLE 2-continued
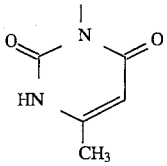 C-164
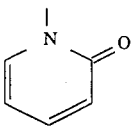 C-165
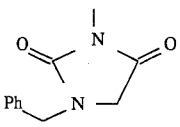 C-166
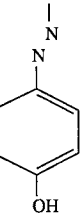 C-167
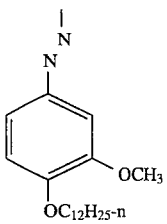 C-168
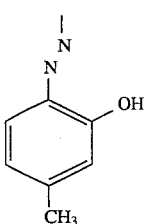 C-169
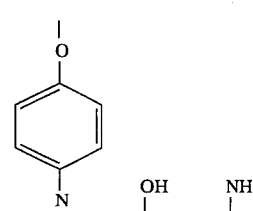 C-170

TABLE 2-continued
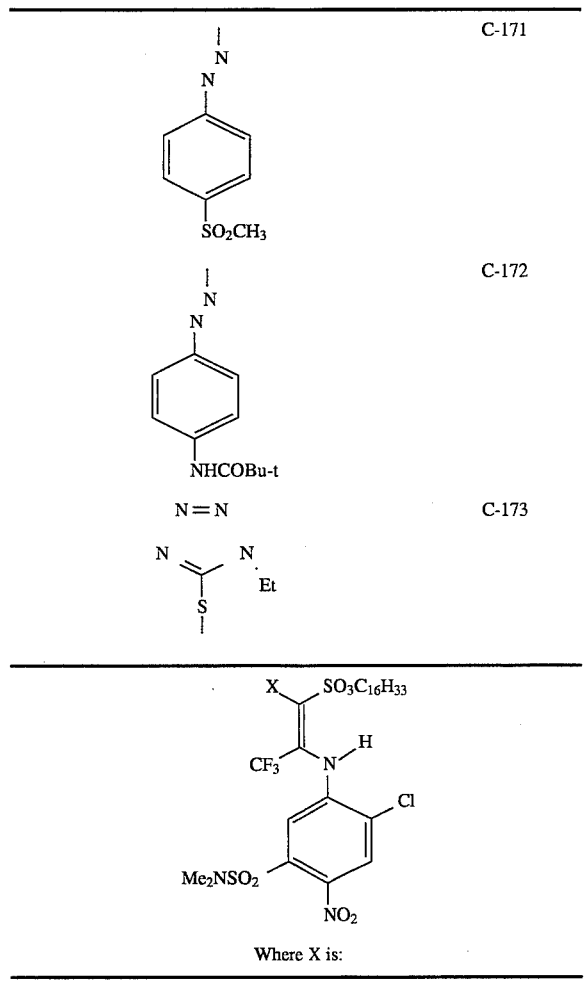
C-171
C-172
C-173
Where X is:
C-174
C-175
C-176
C-177
TABLE 2-continued
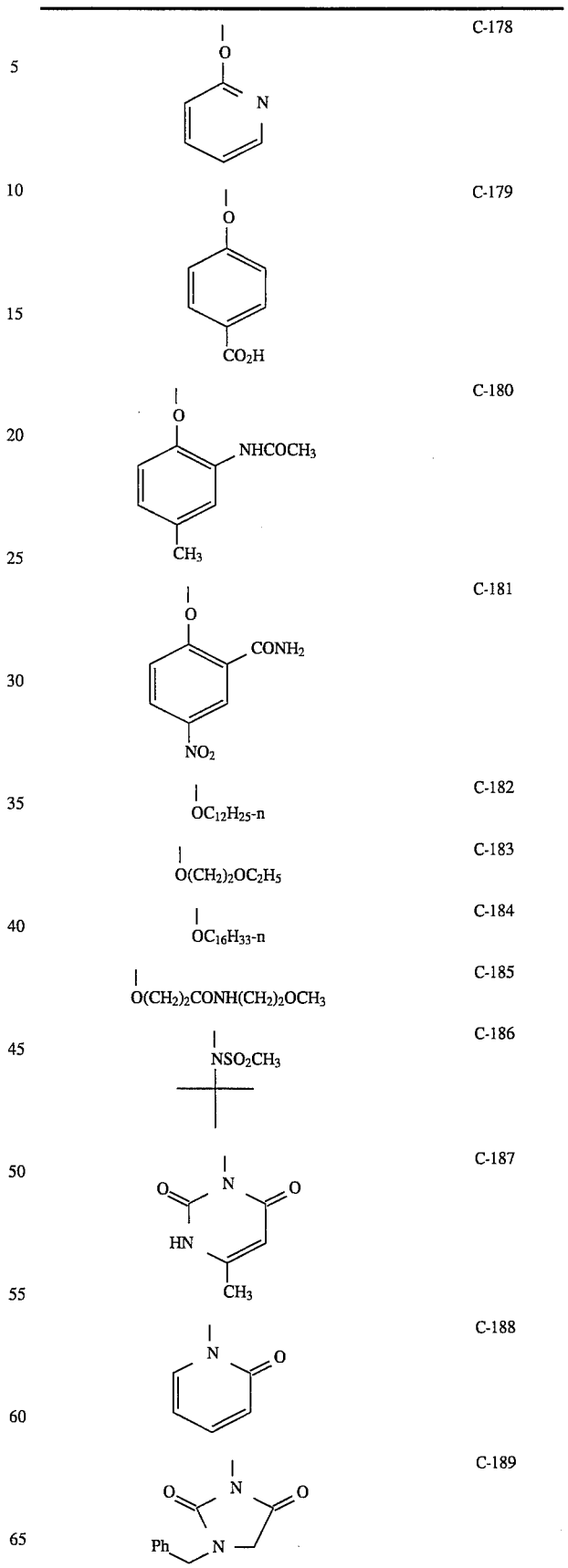
C-178
C-179
C-180
C-181
C-182
C-183
C-184
C-185
C-186
C-187
C-188
C-189

TABLE 2-continued
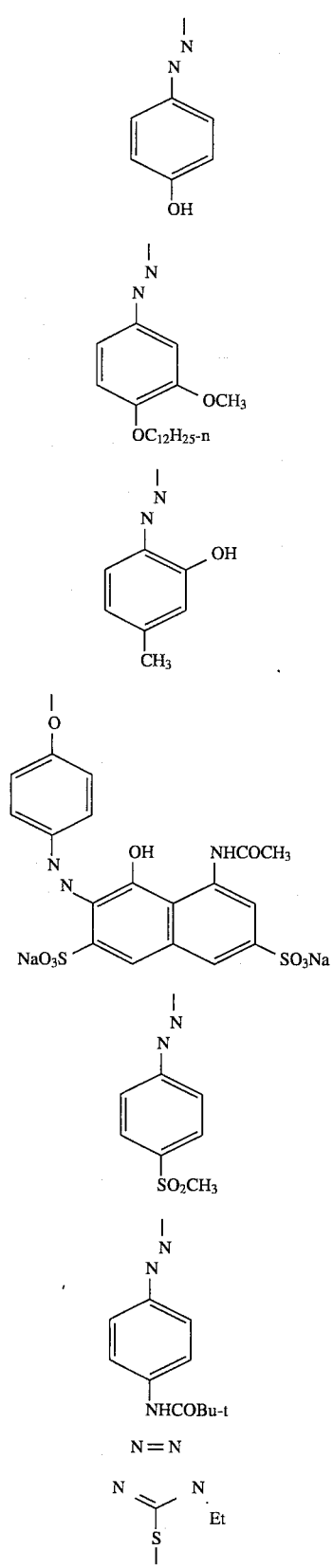
TABLE 2-continued
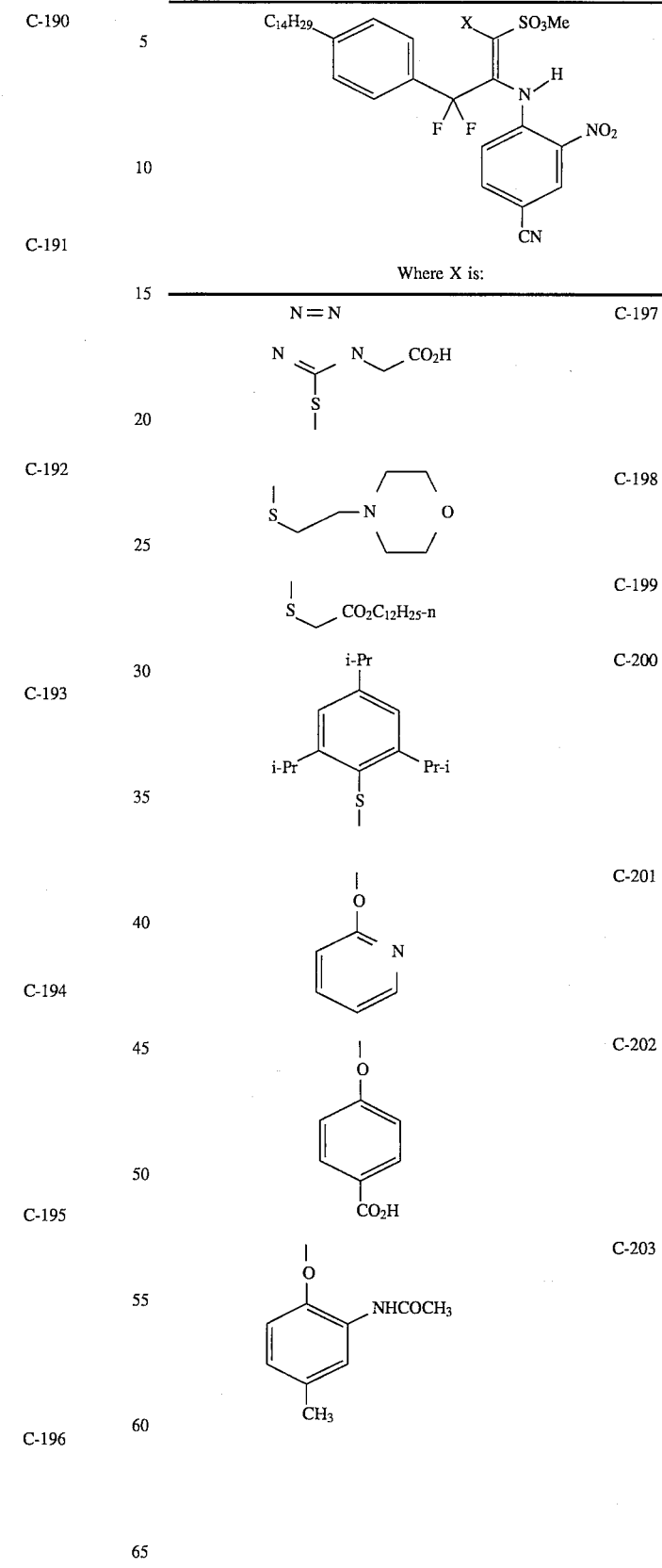

TABLE 2-continued

| | |
|---|---|
| 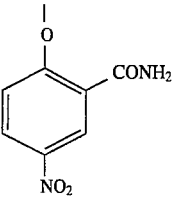 | C-204 |
| 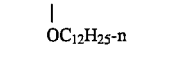 | C-205 |
| 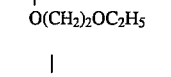 | C-206 |
| 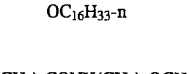 | C-207 |
| 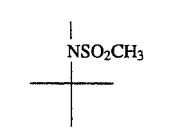 | C-208 |
|  | C-209 |
| 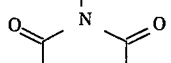 | C-210 |
| 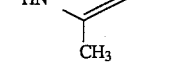 | C-211 |
| 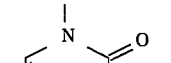 | C-212 |
| 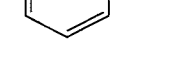 | C-213 |
| 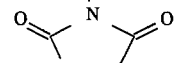 | C-214 |
| 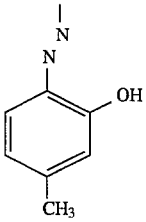 | C-215 |
| 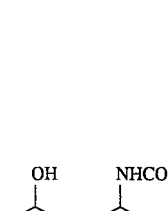 | C-216 |
| 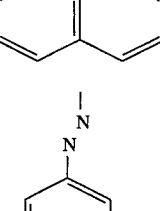 | C-217 |
| 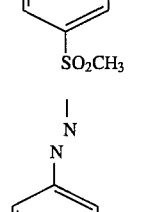 | C-218 |
| 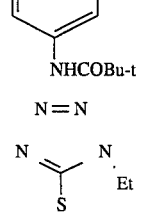 | C-219 |

As used herein, substituted or the term substituent, unless otherwise specifically stated, has a broad definition. The substituent may be, for example, halogen, such as chlorine, bromine or fluorine; nitro; hydroxyl; cyano; and —CO$_2$H and its salts; and groups which may be further substituted, such as alkyl, including straight or branched chain alkyl, such as methyl, trifluoromethyl, ethyl, t-butyl, 3-(2,4-di-t-amylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-( 2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, α- or β-naphthyloxy, and 4-tolyloxy; carbonamido, such as acetamido, benzamido, butyramido, tetradecanamido, α-(2,4-di-t-pentyl-phenoxy)acetamido, α-(2,4-di-t-pentylphenoxy)butyramido, pentadecylphenoxy)-hexanamido, α-(4-hydroxy-3-t-butylphenoxy)-tetradecanamido, 2-oxo-pyrrolidin-1-yl, 2-oxo-5-tetradecyl-pyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylcarbonylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N, N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, and hexadecylsulfonamido; sulfamoyl, such as N-methylsulfamoyl, N,N-dipropylsulfamoylamino, N-ethylsulfamoyl, N,N-dipropylsulfamoyl, N-hexadecylsulfamoyl, N, N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-( 2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; azo, such as phenylazo and naphthylazo; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

The particular substituents used may be selected to attain the desired photographic properties for a specific application and can include, for example, hydrophobic groups, solubilizing groups, blocking groups, etc. Generally, the above groups and substituents thereof may typically include those having 1 to 42 carbon atoms and typically less than 30 carbon atoms, but greater numbers are possible depending on the particular substituents selected. Moreover, as indicated, the substituents may themselves be suitably substituted with any of the above groups.

The materias of the invention can be used in any of the ways and in any of the combinations known in the art. Typically, the invention materials are incorporated in a silver halide emulsion and the emulsion coated as a layer on a support to form part of a photographic element. Alternatively, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in the component molecule. Representative ballast groups include substituted or unsubstituted alkyl or aryl groups containing 8 to 42 carbon atoms. Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arysulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in Research Disclosure, November 1992, Item 34390 published by Kenneth Mason Publications, Ltd., Dudley Annex, 12a North Street, Emsworth, Hampshire P010 7DQ, ENGLAND.

In the following discussion of suitable materials for use in the emulsions and elements of this invention, reference will be made to Research Disclosure, December 1989, Item 308119, available as described above, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections VII and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895, 826, 3,002,836, 3,034,892, 3,041,236, 4,333,999, 4,883,746 and "Farbkuppler-eine LiteratureUbersicht," published in Agfa Mitteilungen, Band III, pp. 156–175 (1961). Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311, 082, 2,343,703, 2,369,489, 2,600,788, 2,908,573, 3,062,653, 3,152,896, 3,519,429, and "Farbkuppler-eine LiteratureUbersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized and color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine LiteratureUbersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. Nos. 4,301,235; 4,853, 319 and 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983, 608; 4,070,191; and 4,273,861; German Applications DE 2,706,117 and DE 2,643,965; U.K. Patent 1,530,272; and Japanese Application A-113935. The masking couplers may be shifted or blocked, if desired.

For example, in a color negative element, the materials of the invention may replace or supplement the materials of an element comprising a support bearing the following layers from top to bottom:

(1) one or more overcoat layers containing ultraviolet absorber(s);

(2) a two-coat yellow pack with a fast yellow layer containing "Coupler 1": Benzoic acid, 4-chloro-3(( 2-(4-ethoxy-2,5-dioxo-3-(phenylmethyl)-1-imidazolidinyl)- 3-(4-methoxyphenyl)-1,3-dioxopropyl)amino)-, dodecyl ester and a slow yellow layer containing the same compound together with "Coupler 2": Propanoic acid, 2-[[5-[[4-[2-[[[2,4bis( 1,1-dimethylpropyl)phenoxy]acetyl]amino]-5[ (2,2,3,3,4,4,4-heptafluoro-1-oxobutyl)amino]-4hydroxyphenoxy]- 2,3-dihydroxy-6-[(propylamino)carbonyl]phenyl]thio]-1,3,4-thiadiazol-2-yl]thio]-, methyl ester and "Coupler 3": 1-((dodecyloxy)carbonyl) ethyl(3-chloro-4-((3-(2-chloro-4-((1-tridecanoylethoxy) carbonyl)anilino)-3-oxo-2-((4)(5)(6)-(phenoxycarbonyl)- 1H-benzotriazol-1-yl)propanoyl)amino))benzoate;

(3) an interlayer containing fine metallic silver;

(4) a triple-coat magenta pack with a fast magenta layer containing "Coupler 4": Benzamide, 3-((2-(2,4-bis( 1,1-dimethylpropyl)phenoxy)-1-oxobutyl)amino)-N-( 4,5-dihydro-5-oxo-l-(2,4,6-trichlorophenyl)-1H-pyrazol- 3-yl)-, "Coupler 5": Benzamide, 3-((2-(2,4bis( 1,1-dimethylpropyl)phenoxy)-1-oxobutyl)amino)-N-( 4',5'-dihydro-5'-oxo-1'-(2,4,6-trichlorophenyl) (1,4'-bi- 1H-pyrazol)-3'-yl)-, "Coupler 6": Carbamic acid, ( 6-(((3-(dodecyloxy)propyl) amino)carbonyl)-5-hydroxy-1-naphthalenyl)-, 2-methylpropyl ester , "Coupler 7": Acetic acid, ((2-((3-(((3-(dodecyloxy)propyl)amino) carbonyl)-4-hydroxy-8-(((2-methylpropoxy)carbonyl) amino)-1-naphthalenyl)oxy)ethyl)thio)-, and "Coupler 8" Benzamide, 3-((2-(2,4-bis(1,1-dimethylpropyl) phenoxy)-1-oxobutyl)amino)-N-(4,5-dihydro-4-((4methoxyphenyl) azo)-5-oxo-1-(2,4,6-trichlorophenyl)-1H-pyrazol- 3-yl)-; a mid-magenta layer and a slow magenta layer each containing "Coupler 9": a ternary copolymer containing by weight in the ratio 1:1:2 2-Propenoic acid butyl ester, styrene, and N-[1-(2,4,6-trichlorophenyl)- 4,5-dihydro-5-oxo-1H-pyrazol-3-yl]-2-methyl-2-propenamide; and "Coupler 10": Tetradecanamide, N-(4-chloro-3-((4-((4-((2,2-dimethyl-1-oxopropyl) amino)phenyl)azo)-4,5-dihydro-5-oxo-1(2,4,6-trichlorophenyl)-1H-pyrazol-3-yl)amino)phenyl)-, in addition to Couplers 3 and 8;

(5) an interlayer;

(6) a triple-coat cyan pack with a fast cyan layer containing Couplers 6 and 7; a mid-cyan containing Coupler 6 and "Coupler 11": 2,7-Naphthalenedisulfonic acid, 5-(acetylamino)-3-((4-(2-(((3-(((3-(2,4-bis(1,1-dimethylpropyl)phenoxy) propyl)amino)carbonyl)-4-hydroxy-1-naphthalenyl) oxy)ethoxy)phenyl)azo)- 4-hydroxy-, disodium salt; and a slow cyan layer containing Couplers 2 and 6;

(7) an undercoat layer containing Coupler 8; and (8) an antihalation layer.

In a color paper format, the materials of the invention may replace or supplement the materials of an element comprising a support bearing the following layers from top to bottom:

(1) one or more overcoats;

(2) a cyan layer containing "Coupler 1": Butanamide, 2-(2,4-bis(1,1-dimethylpropyl)phenoxy)-N-( 3,5-dichloro-2-hydroxy-4-methylphenyl)-, "Coupler 2": Acetamide, 2-(2,4-bis(1,1-dimethylpropyl)phenoxy)-N-( 3,5-dichloro-2-hydroxy-4-, and UV Stabilizers: Phenol, 2-(5-chloro-2H-benzotriazol-2-yl)-4,6-bis( 1,1-dimethylethyl)-;Phenol, 2-(2H-benzotriazol-2-yl)-4(1,1-dimethylethyl)-;Phenol, 2-(2H-benzotriazol-2-yl) 4-(1,1-dimethylethyl)-6-(1-methylpropyl)-; and Phenol, 2-(2H-benzotriazol-2-yl)-4,6-bis(1,1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[ 2-(7-chloro-6-methyl-1H-pyrazolo[1,5-b][1,2,4]triazol-2-yl)propyl]- together with 1,1'-Spirobi(1H-indene), 2,2',3,3'-tetrahydro-3,3,3',3'-tetramethyl-5,5',6,6,'-tetrapropoxy-;

(5) an interlayer; and (6) a yellow layer sonraining "Coupler 4": 1-Imidazolidineacetamide, N-(5-((2-(2,4-bis(1,1-dimethylpropyl)phenoxy)- 1-oxobutyl)amino)-2-chlorophenyl)-.alpha.-( 2,2-dimethyl-1-oxopropyl)-4-ethoxy-2,5-dioxo-3-(phenylmethyl)-.

In a reversal format, the materials of the invention may replace or supplement the materials of an element comprising a support bearing the following layers from top to bottom:

(1) one or more overcoat layers;

(2) a nonsensitized silver halide containing layer;

(3) a triple-coat yellow layer pack with a fast yellow layer containing "Coupler 1": Benzoic acid, 4-( 1-(((2-chloro-5-((dodecylsulfonyl)amino)phenyl) amino)carbonyl)-3,3-dimethyl-2-oxobutoxy)-, 1methylethyl ester; a mid yellow layer containing Coupler 1 and "Coupler 2": Benzoic acid, 4-chloro- 3-[[2-[4-ethoxy-2,5-dioxo-3-(phenylmethyl)- 1-imidazolidinyl]-4,4-dimethyl-1,3-dioxopentyl]amino]-, dodecylester; and a slow yellow layer also containing Coupler 2;

(4) an interlayer;

(5) a layer of fine-grained silver;

(6) an interlayer;

(7) a triple-coated magenta pack with a fast magenta layer containing "Coupler 3": 2-Propenoic acid, butyl ester, polymer with N-[1-(2,5-dichlorophenyl)- 4,5-dihydro-5-oxo-1H-pyrazol-3-yl]-2-methyl- 2-propenamide; "Coupler 4": Benzamide, 3-((2-(2,4bis( 1,1-dimethylpropyl)phenoxy)-1-oxobutyl)amino)-N( 4,5-dihydro-5-oxo-1-(2,4,6-trichlorophenyl)-1H-pyrazol- 3-yl)-; and "Coupler 5": Benzamide, 3-(((2,4bis( 1,1-dimethylpropyl)phenoxy)acetyl)amino)-N-(4,5-dihydro-5-oxo-1-(2,4,6-trichlorophenyl)-1H-pyrazol-3-yl)-; and containing the stabilizer 1,1'-Spirobi(1H-indene), 2,2',3,3'-tetrahydro-3,3,3',3'-tetramethyl- 5,5',6,6'-tetrapropoxy-; and in the slow magenta layer Couplers 4 and 5 with the same stabilizer;

(8) one or more interlayers possibly including fine-grained nonsensitized silver halide;

(9) a triple-coated cyan pack with a fast cyan layer containing "Coupler 6": Tetradecanamide, 2-( 2-cyanophenoxy)-N-(4-((2,2,3,3,4,4,4-heptafluoro- 1-oxobutyl)amino)-3-hydroxyphenyl)-; a mid cyan containing "Coupler 7": Butanamide, N-(4-((2-(2,4-bis( 1,1-dimethylpropyl)phenoxy)-1-oxobutyl)amino)-2-hydroxyphenyl)- 2,2,3,3,4,4,4-heptafluoro- and "Coupler 8": Hexanamide, 2-(2,4-bis(1,1-dimethylpropyl)phenoxy)-N-( 4-((2,2,3,3,4,4,4-heptafluoro-1-oxobutyl)amino)-3-hydroxyphenyl)-;

(10) one or more interlayers possibly including fine-grained nonsensitized silver halide; and

(11) an antihalation layer.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. Nos. 4,163, 669; 4,865,956; and 4,923,784, may be useful. Also contemplated is use of the compositions in association with nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non colorforming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the compositions may be blocked or coated in protected form as described, for example, in Japanese Application 61/258,249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384, 657; 3,379,529; 3,615,506; 3,617,291; 3,620,746; 3,701, 783; 3,733,201; 4,049,455; 4,095,984; 4,126,459; 4,149, 886; 4,150,228; 4,211,562; 4,248,962; 4,259,437; 4,362, 878; 4,409,323; 4,477,563; 4,782,012; 4,962,018; 4,500, 634; 4,579,816; 4,607,004; 4,618,571; 4,678,739; 4,746, 600; 4,746,601; 4,791,049; 4,857,447; 4,865,959; 4,880, 342; 4,886,736; 4,937,179; 4,946,767; 4,948,716; 4,952, 485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 72,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazotes. In a preferred embodiment, the inhibitor moiety or group is selected from the following formulas:

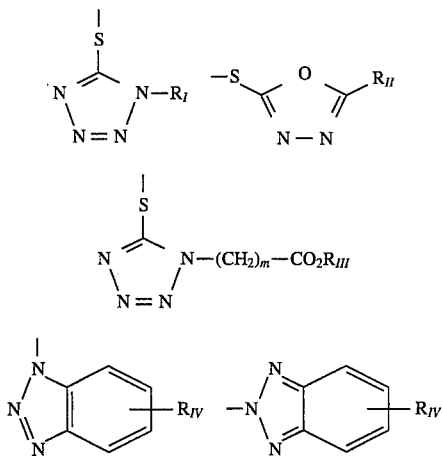

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and $-SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, $-COOR_V$ and $-NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group, which produces the time-delayed release of the inhibitor group such as groups utilizing the cleavage reaction of a hemiacetal (U.S. Pat. No. 4,146,396, Japanese Applications 60- 249148; 60-249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. Nos. 4,438,193; 4,618,571) and groups that combine the features describe above. It is typical that the timing group or moiety is of one of the formulas:

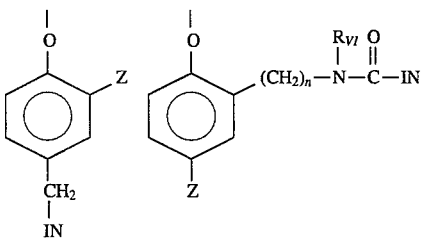

wherein IN is the inhibitor moiety, Z is selected from the group consisting of nitro, cyano, alkylsulfonyl; sulfamoyl ($-SO_2NR_2$); and sulfonamido ($-NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

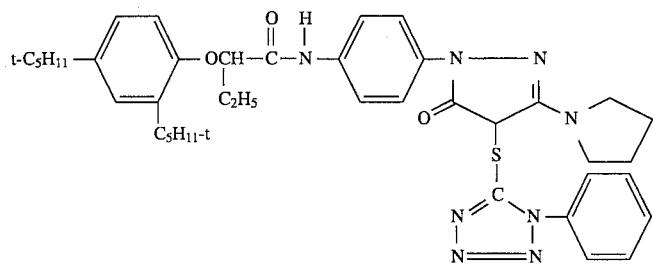
D1
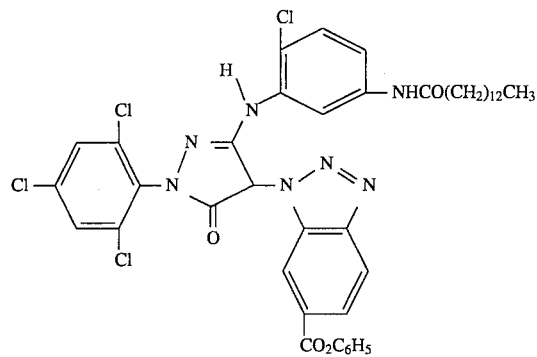
D2
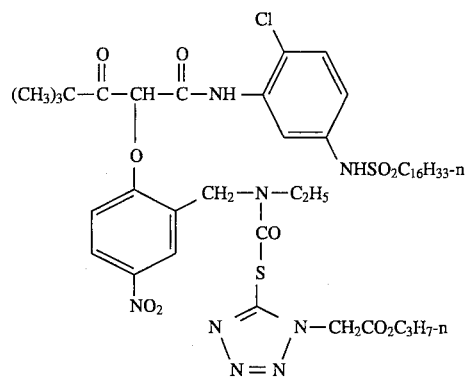
D3
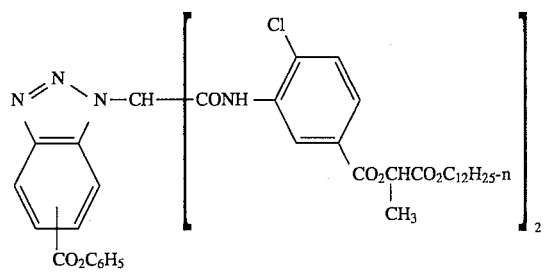
D4
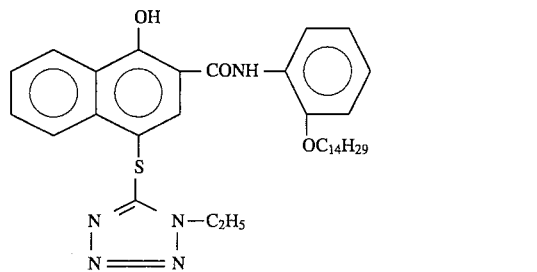
D5

-continued
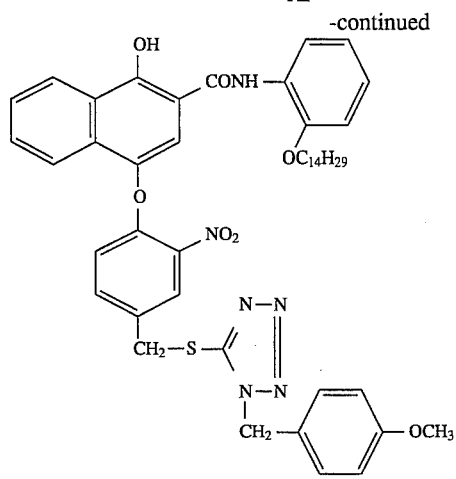
D6
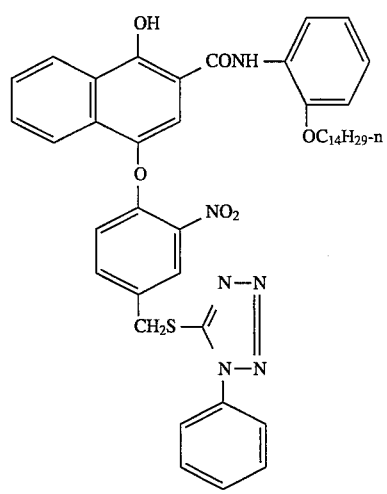
D7
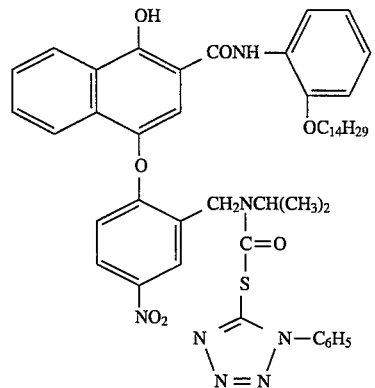
D8

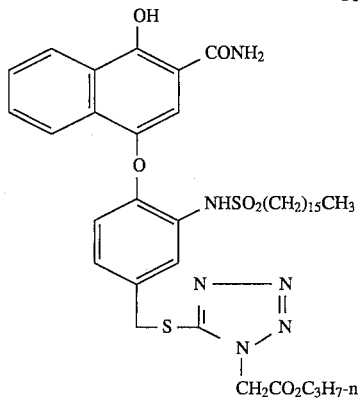

D9

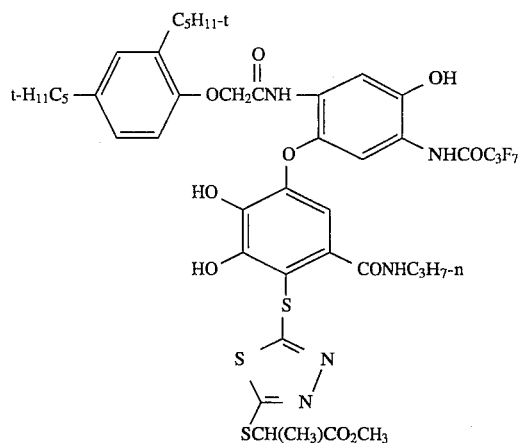

D10

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90- 072,632; 90-072,633; 90-072,634; 90-077,822; 90- 078,229; 90-078,230; 90-079,336; 90-079,337; 90- 079,338; 90-079,690; 90-079,691; 90-080,487; 90- 080,488; 90-080,489; 90-080,490; 90-080,491; 90-080,492; 90-080,494; 90-085,928; 90-086,669; 90- 086,670; 90-087,360; 90-087,361; 90-087,362; 90- 087,363; 90-087,364; 90-088,097; 90-093,662; 90- 093,663; 90-093,664; 90-093,665; 90-093,666; 90- 093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. The described elements can be processed in the known C-41 color process as described in The British Journal of Photography Annual of 1988, pages 191–198. Where applicable, the element may be processed in accordance with color print processes such a the RA-4 process of Eastman Kodak Company as described in the British Journal of Photography Annual of 1988, Pp 198–199. To provide a positive (or reversal) image, the color development step can be preceded by development with a non-chromogenic developing agent to develop exposed silver halide, but not form dye, and followed by uniformly fogging the element to render unexposed silver halide developable. Alternatively, a direct positive emulsion can be employed to obtain a positive image.

Preferred color developing agents are p-phenylenediamines such as:
4-amino-N,N-diethylaniline hydrochloride,
4-amino-3-methyl-N,N-diethylaniline hydrochloride,
4-amino-3-methyl-N-ethyl-N-(β-(methanesulfonamido) ethyl)aniline sesquisulfate hydrate,
4-amino-3-methyl-N-ethyl-N-(β-hydroxyethyl)aniline sulfate,
4-amino-3-β-(methanesulfonamido)ethyl-N,N-diethylaniline hydrochloride and
4-amino-N-ethyl-N-(2-methoxyethyl)-m-toluidine di-p-toluene sulfonic acid.

Development is usually followed by the conventional steps of bleaching, fixing, or bleachfixing, to remove silver or silver halide, washing, and drying.

It is understood thoroughout this specification and claims that any reference to a substituent by the identification of a group containing a substitutable hydrogen (e.g. alkyl, amine, aryl, alkoxy, heterocyclic, etc.), unless otherwise specifically stated, shall encompass not only the substituent's unsubstituted form, but also its form further substituted with any photographically useful substituents. Usually the further substituent will have less than 30 carbon atoms and typically less than 20 carbon atoms.

The following Examples are included for a better understanding of the invention.

EXAMPLE 1

Preparation of
2-(N-(2-Cyano-4-(dodecylsulphonyl)-anilino)) - 2-trifluoromethylacrylacrylonitrile

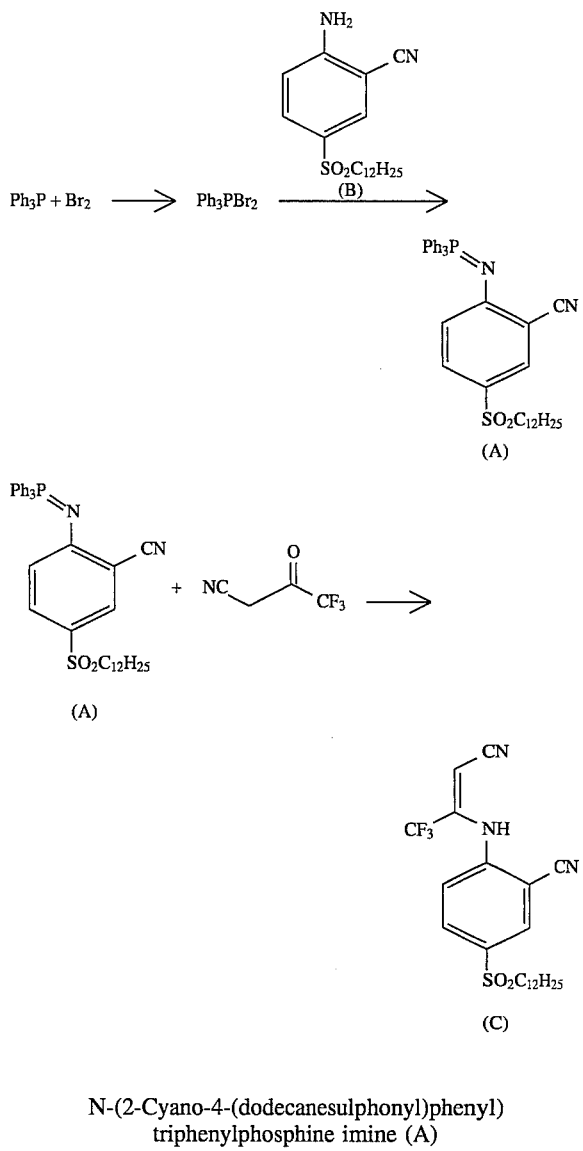

N-(2-Cyano-4-(dodecanesulphonyl)phenyl) triphenylphosphine imine (A)

Bromine (0.62 g, 3.88 mmol) in 1,2-dichloroethane (3 ml) was added dropwise to stirred solution of triphenylphoshine (1.01 g, 3.85 mmol) in 1,2-dichloroethane (30 ml) under a nitrogen atmosphere. The temperature of the reaction was maintained at less than 5° C. by the use of an ice/water bath.

After the addition was complete a mixture of the aniline B (0.90 g, 2.57 mmol) and triethylamine (0.78 g, 7.72 mmol) in warm 1,2-dichloroethane (25 ml) was added in one portion to the suspension and the mixture heated to reflux. After being heated at reflux for 1 hour the solution was allowed to cool to room temperature and the solid was filtered-off. Concentration of the filtrate in vacuo gave an oil which crystallised upon standing. This solid was suspended in hot ethyl acetate, filtered and allowed to cool to give the product (0.95 g, 1.56 mmol, 61%) as a white crystalline solid. All spectroscopic data is consistent with the proposed structure.

2-(N-(2-Cyano-4-(dodecylsulphonyl)-anilino))-2trifluoromethylacrylonitrile (C)

A mixture of the phosphine imine A (0.80 g, 1.31 mmol) and 3-cyano-1,1,1-trifluoroacetone (0.23 g, 1.68 mmol) was heated rapidly to reflux in 1,2-dichloroethane (10 ml). After 2 hours the slightly cloudy solution was concentrated in vacuo to give a yellow oil (1.07 g) which was purified by column chromatography over silica (eluent 2:1 60–80 petroleum ether/ethyl acetate) to give the product (0.42 g, 0.896 mmol, 68 %) as a white solid. All spectroscopic data is consistent with the proposed structure.

phonic acid (catalytic amount) in toluene (10 ml) was heated at reflux, slowly allowing the toluene to distill off. After 2 hours the reaction was allowed to cool and then concentrated in vacuo to give a brown oily-solid. This was purified by column chromatography over silica (eluent 3:1 60–80 petroleum ether/ethyl acetate) to give the product (0,112 g, 0.436 mmol, 6%) as a yellow oil which crystallised upon standing. All spectroscopic data is consistent with the proposed structure.

EXAMPLE 3

Compound C-1 of the present invention and control compound A were incorporated into a photographic silver bromoiodide emulsion and coated in the following format:

| Support - Cellulose acetate | |
|---|---|
| Gel Supercoat | |
| Gelatin | 1.50 gm/m$^2$ |
| Emulsion Layer | |
| Silver bromoiodide | 1.61 gm/m$^2$ |
| Coupler | 1.04 mmol/m$^2$ |
| Gelatin | 2.42 gm/m$^2$ |
| Bis(vinylsulphonyl)methane (hardener) | 0.06 gm/m$^2$ |

Control compound A had the following formula:

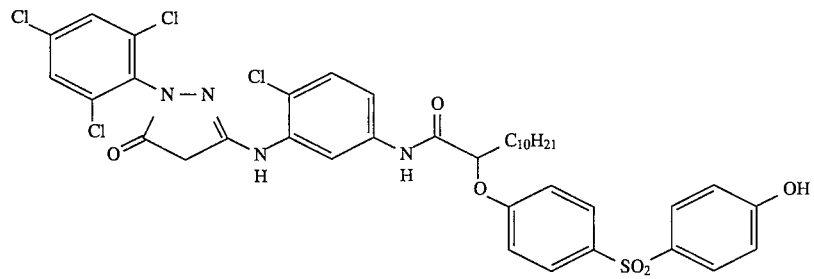

EXAMPLE 2

Preparation of 2-(N-(3-nitroanilino))-2-trifluoromethylacrylonitrile

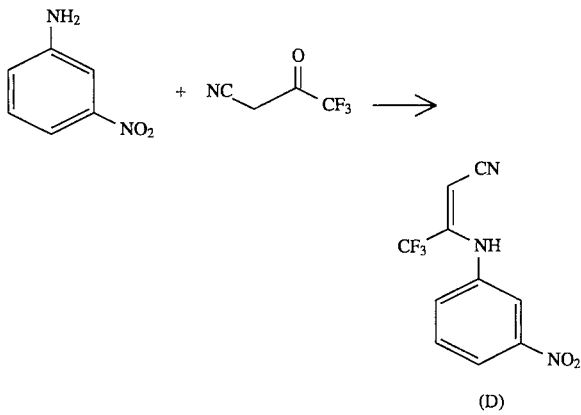

2-(N-(3-nitroanilino))-2-trifluoromethylacrylonitrile (D)

A mixture of m-nitroaniline (0.94 g, 6.81 mmol), 3-cyano-1,1,1-trifluoroacetone (0.93 g, 6.79 mmol and p-toluenesul- The coupler dispersion used contained 6% w/w gelatin, 8.8% coupler and coupler solvents in the ratio:- coupler:tricresyl phosphate: 2-(2butoxyethoxy) ethyl acetate 1.0:0.5:1.5 (w/w). The auxiliary solvent (2-(2-butoxyethoxy)ethyl acetate) was removed by washing the dispersion for 6 hours at 4° C. and pH 6.0.

Spectrophotometric testing

The experimental photographic coatings prepared in this way were slit and chopped into 30 cm×35 mm test strips. These strips were exposed (0.1 sec) through a 0-0.9ND step-wedge (0.3ND steps) test object and Daylight V, Wratten 9 filters and the correct ND filters to give an optical density of about 1.0. The strips were processed through a C-41 process as described in the British Journal of Photography (1988) 196–198 using the following process times:

| Developer | 2.5 minutes |
|---|---|
| Bleach | 4.0 minutes |
| Wash | 2.0 minutes |
| Fix | 4.0 minutes |
| Wash | 2.0 minutes | and samples cut from the magenta dye image step with density closest to 1.0. Visible absorption spectra (normalised to 1.0 density) were obtained using a PyeUnicam SP8-100 spectrophotometer. Dye hues are expressed in terms of the wavelength of maximum absorption ($\lambda_{max}$).

| Results | |
|---|---|
| Coupler | $\lambda max/nm$ |
| A | 546.0 |
| C-1 | 548.5 |

Coupler C-1 had very similar spectral absorption properties as known coupler A.

What is claimed is:

1. A photographic element comprising a support, at least one photosensitive silver halide layer and in or adjacent said silver halide layer a colour coupler of one of the general formulas:

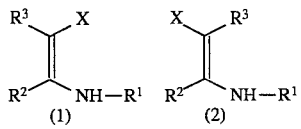

wherein $R^1$ is a substituted or unsubstituted aryl or a substituted or unsubstituted heterocylic group, $R^2$ is a saturated or unsaturated, primary or secondary alkyl group in which the carbon atom which joins $R^2$ to the rest of the coupler has at least one fluorine atom attached to it, $R^3$ is an electron-withdrawing group, and X is H or a coupling-off group, and wherein the electron-withdrawing properties of $R^1$ are such that the dye formed on coupling with oxidised colour developing agent 4-(N-ethyl-N-2-hydroxyethyl)-2-methylphenylenediamine has a $\lambda_{max}$ of from 537 to 570 nm.

2. A photographic element as claimed in claim 1 in which $R^1$ is substituted with an electron-withdrawing substitutent.

3. A photographic element as claimed in claim 1 in which $R^1$ is substituted with a cyano, nitro, alkylsulphonyl or arylsulphonyl group.

4. A photographic element as claimed in claim 1 in which $R^2$ is a trifluoromethyl, 2,2,2-trifluoroethyl, nonafluorobutyl or trifluoroethylene group.

5. A photographic element as claimed in claim 1 in which $R^3$ is halogen, —CN, —NO$_2$, —OR$^4$, —SR$^4$, —SO$_2$R$^5$, —OSO$_2$R$^5$, —SOR$^5$, —NHCOR$^5$, —CONHR$^5$, —OCONHR$^5$, —NHCO—OR$^5$, —SO$_2$NH—R$^5$, —NHSO$_2$R$^5$, —NHSO$_2$NHR$^5$, —NHNH—SO$_2$—R$^5$, —COOH, —COOR$^5$, —O—COR$^5$, —COR$^5$, —CSR$^5$, —CONHNHR$^5$, —CF$_3$, —NH$_2$, —NHR$^5$, —NHR$^5$R$^{5'}$, silyloxy, aryl, aralkyl, alkyl, cycloalkyl, ureido, imido, or a heterocycle, wherein $R^5$ is an alkyl, cycloalkyl, aryl or heterocyclic group any of which may be substituted, $R^{5'}$ has the same definition as $R^5$ and may be the same as or different from $R^5$, and $R^4$ is an alkyl, cycloalkyl, aryl or heterocyclic group, any of which are optionally substituted, and wherein the nature of the groups $R^5$, $R^{5'}$ and $R^4$ and the substituents thereon are such that the group is electron-withdrawing.

6. A photographic element as claimed in claim 1 in which X is hydrogen, chloro, alkoxy, phenyloxy, 2-chloro-, 2,3,5-isopropyl-, 4-carboxy-, 4-carboxy-2-methyl-carbonamido, 4-nitro-2-carbamoyl-phenyloxy, alkylthio, phenylthio, or 2,3,5-isopropyl-phenylthio, pyridyloxy, sulfonyloxy, acyloxy, carboxy, acyl, 2-pyridyl, sulfonamido, mercaptotetrazolyl, mercaptopropionoyl, phosphonyloxy or 4-hydroxy-, 4-hexadecyloxy- 3-methoxy- 4-methyl-2-hydroxy-, 4-methylsulphonyl-, or 4-t-butylcarbonamido-phenylazo.

7. The element of claim 1 wherein $R^2$ is further substituted by one or more additional fluoride atoms on the carbon atom which joins $R^2$ to the rest of the coupler.

8. A process for forming an image in an element as described in claim 1 after said element has been exposed to light comprising contacting said element with a color developing agent.

9. The process of claim 8 wherein said exposed element is subjected to a reversal color development process.

* * * * *